US Patent Number: 5,036,052
Date of Patent: Jul. 30, 1991

Ozeki et al.

[54] AMINO ACID NUTRIENT COMPOSITIONS

[75] Inventors: Kohji Ozeki; Yoshitsugu Tsukamoto; Hideya Yaginuma, all of Shiga; Makoto Sato, Moriyama, all of Japan

[73] Assignees: Morishita Pharmaceutical Co., Ltd., Osaka; Ajinomoto Co., Inc., Tokyo, both of Japan

[21] Appl. No.: 369,123

[22] Filed: Jun. 21, 1989

[30] Foreign Application Priority Data

Jun. 22, 1988 [JP] Japan .................. 63-155744
Aug. 26, 1988 [JP] Japan .................. 63-212758
Oct. 25, 1988 [JP] Japan .................. 63-270558
Oct. 28, 1988 [JP] Japan .................. 63-273826
Dec. 7, 1988 [JP] Japan .................. 63-310772

[51] Int. Cl.$^5$ .................. A61K 31/00; A61K 31/415; A61K 31/40; A61K 31/195
[52] U.S. Cl. .................. 514/19; 514/400; 514/419; 514/423; 514/561; 514/562; 514/564; 514/565; 514/566; 514/2
[58] Field of Search .................. 514/2, 561, 19, 400, 514/419, 423, 562, 564, 565, 566

[56] References Cited

U.S. PATENT DOCUMENTS 3,701,666 10/1972 Winitz .................. 514/561
4,340,592 7/1982 Adibi .
4,780,475 10/1988 Cerra et al. .................. 514/561
4,792,549 12/1988 Takahashi et al. .................. 514/400

FOREIGN PATENT DOCUMENTS 0182356 5/1986 European Pat. Off. .

OTHER PUBLICATIONS

Patent Abstracts of Japan, vol. 10, No. 103, Apr. 1986.
Patent Abstracts of Japan, vol. 5, No. 54, Apr. 1981.
Patent Abstracts of Japan, vol. 11, No. 381, Dec. 1987.
Patent Abstracts of Japan, vol. 10, No. 144, May 1986.

Primary Examiner—Frederick E. Waddell
Assistant Examiner—Raymond J. Henley
Attorney, Agent, or Firm—Oblon, Spivak, McClelland, Maier & Neustadt

[57] ABSTRACT

There are herein disclosed stablized and/or dense L-amino acid nutrient compositions, i.e., amino acid infusion solutions, which contain at least one oligopeptide having at least one residue of L-Tryptophan, L-Tyrosine, L-Leucine, L-Isoleucine and L-Valine.

2 Claims, No Drawings

AMINO ACID NUTRIENT COMPOSITIONS

BACKGROUND OF THE INVENTION

1. Field of the Invention:

The present invention provides stabilized and/or dense L-amino acid nutrient compositions. Such stabilized and/or dense L-amino acid nutrient compositions may be prepared by using oligopeptides whose molecules contain at least one L-amino acid residue of some specific L-amino acids.

2. Discussion of the Background:

When patients cannot orally take, or can take orally but in an insufficient amount of, amino acids or protein in various diseases or in preoperative or postoperative stage, etc. in spite of necessity to take them, L-amino acid nutrient compositions whose main ingredients are L-amino acids, e.g., L-amino acid infusion solutions for intravenous administration (referred to hereinafter as "amino acid infusion solutions") have been widely utilized for the purpose of nutrient supplementation.

In general, however, amino acid infusion solutions tend to form degradation products with the passage of time and color to yellow. Therefore, for the purpose of preventing coloration, etc., i.e., as stabilizers, there have been hitherto used inorganic salts of sulfurous acid or pyrosulfurous acid such as sodium hydrogensulfite, potassium hydrogensulfite, sodium sulfite, potassium sulfite, sodium pyrosulfite, potassium pyrosulfite, etc. A method for stabilization using sulfurous acid salts of basic amino acids is also disclosed (Japanese Patent Application Laid-Open No. 49-102831). These hydrogensulfites or sulfites are very effective for preventing coloration of amino acid infusion solutions. Among them, hydrogensulfites are superior.

However, it is known that the hydrogensulfites and sulfites react with amino acids. They are very reactive, in particular, with cystine, methionine or tryptophan. For example, these salts react with cystine to cleave the disulfide bond and give cysteine thiosulfate. Furthermore, the salts react with methionine in the presence of oxygen to form methionine sulfoxide. The salts cause an extremely complicated reaction with tryptophan and the major reaction products are highly reactive formylkynurenine, 2,3-dioxyindolealanine, etc. As such, these salts are effective for apparent prevention of coloration of amino acid infusion solutions but give reaction products which are harmful to the living body. Moreover, the hydrogensulfites or sulfites react with protein to cleave disulfide bond or bind to protein itself when they are taken into the living body. Furthermore, the salts also react with nucleic acid bases or other compounds in the living body and are known to have a potent mutagenecity.

Accordingly, it is not preferred to use the hydrogensulfites or sulfites as stabilizers for amino acid infusion solutions. However, no stabilizers better than these salts are known so that the prior art cannot help using the salts in a trace amount under the actual situation.

It has been now found that the prime cause of instability such as coloration, etc. of amino acid infusion solutions is attributable to L-tryptophan (Trp) and the coloration is proportional to the concentration of Trp in amino acid infusion solutions. Trp is one of essential amino acids. It is known that Trp greatly affects protein synthesis in liver and it has been a demand to increase the Trp concentration in an amino acid infusion solution. As already stated, however, there have been serious problems in preparation of amino acid infusion solutions that an increase in the Trp concentration results in increased coloration and the like.

A first problem to be solved by the present invention is, under the above-described prior art, to provide stable, L-amino acid-containing nutrient aqueous compositions which contain the Trp ingredient in a desirable amount but no stabilizers such as hydrogensulfites or sulfites conventionally used.

On the other hand, recently, since researches on the amino acid metabolism under the sick conditions have been promoted and hence the roles of the various amino acids under the sick conditions have been made clear, the stream of the development of the amino acid infusion solutions is divided into two directions, that is, the development of amino acid infusion solutions according to the respective sick conditions taking the therapeutic aspect into consideration on one hand and the development of general-purpose amino acid infusion solutions for correcting the nutrient characteristics relatively common to the various sick conditions on the other hand.

Among L-amino acids used for amino acid infusion solutions, L-tyrosine (Tyr) has been proven essential for liver diseases, uremia, immature infants, newborns, etc. Inter alia, with uremia patients, especially Tyr indicates a low level. This is due to that the activity of L-phenylalanine (Phe) hydroxylase is low and thus that the production of Tyr from Phe is inadequate. The decrease in the protein synthesis due to the Tyr deficiency has been recognized to extremely lower the nutrient conditions of the patient. Further, since Tyr is a precursor to catecholamine, it is also indicated that if this is inadequate, various neurosis signs are brought about, and with these patients, Tyr has been gradually taking the position as an essential amino acid. For that reason, it is the present situation that an amino acid infusion solution in which Tyr is formulated so as to adapt to these sick conditions has been sought. However, the solubility of Tyr in water is merely 0.045 g/dl at 25° C., and it is difficult to freely formulate a necessary amount thereof as an ingredient for infusion solution.

As regards the formulation of Tyr in infusion solutions, compositions based on nutrient formulations for healthy humans have heretofore been used, for example, those based on amino acid compositions of human milk or the whole egg according to the report of FAO special committee, 1957. etc. However, as described earlier, with healthy humans Tyr can be synthesized in an adequate amount from Phe, but such synthesis is impossible with certain sick conditions and thus Tyr is positioned as an essential amino acid. Therefore, it is evident that the nutrient formulation for these patients is different from the nutrient formulation for healthy humans.

The formulation for sick conditions taking this into consideration is disclosed in Japanese Patent Application Laid-Open No. 59-16187, where it is indicated that favorable results are obtained when Tyr is contained in the range of 1/12 - 1/17 based on Phe and at a concentration of 0.45–0.55 g/l. However, according to the research on the metabolism of the ingested essential amino acid Phe in vivo, it has been discovered that 50–70 % of the ingested Phe has been converted into Tyr. It is thought that Phe must be present at a concentration of 5.0–10.0 g/l in an ordinary amino acid infusion solution. Even by simple calculation considering the conversion rate described above, it may be presumed that the part 2.5–7.0 g/l of Phe in the formulation must be replaced by Tyr under sick conditions. When this is taken into consideration, the formulation presented in Japanese Patent Application Laid-Open No. 59-16187 has been designed in the range of Tyr solubility, and it seems uncertain that the sick conditions are well considered. On the other hand, no amino acid infusion solutions containing such a high concentration of Tyr have been known.

In the meantime, several methods for increasing the concentration of Tyr have been proposed. Japanese Patent Application Laid-Open No. 56-8312 discloses a method which utilizes peptides such as L-alanyl-L-tyrosine, L-arginyl-L-tyrosine, L-tyrosyl-L-arginine etc., Japanese Patent Application Laid-Open No. 61-247354 discloses glycyl-L-tyrosine and L-alanyl-L-tyrosine and Japanese Patent Application Laid-Open No.62-151156 discloses L-aspartyl-L-tyrosine. However, any of these seems uncertain that the formulations of Tyr are fully studied.

A second problem to be solved by the present invention is, under the above-described prior art, to present an amino acid nutrient infusion composition of a new formulation which contains sparingly soluble tyrosine in an amount necessary at a ratio achieving the purpose without being subject to the pharmaceutical restrictions and also can exert an excellent nutrient effect to the various intended diseases.

As has been discussed earlier, recently, studies on amino acid metabolism under morbid conditions have been advanced, and have revealed the roles of various amino acids under pathological conditions, as a result of which the trend of developing amino acid infusion solutions is divided into two directions: one is to pursue amino acid infusion solutions used in respective diseases laying a stress on therapy and another is to pursue all-purpose amino acid infusion solutions with an attempt to correct nutritious imbalance relatively common to various morbid conditions.

With respect to the branched chain L-amino acids (BCAA) of L-leucine (Leu), L-isoleucine (Ile) and L-valine (Val) among L-amino acids used in amino acid infusion solutions, their sitological significance has been clarified over wide areas including application to surgical seizures, hepatic insufficiency, renal insufficiency, septicemia, premature infant, etc. For development of infusion solutions in either direction described above, attention has been drawn to these amino acids as one of the most important amino acid group. It is known that unlike other amino acids, the branched chain L-amino acids are metabolized mainly in tissues other than liver, and,in particular, Leu has an activity to accelerate synthesis of muscular protein and prevent its decomposition. It is also known that when the branched chain amino acids have been administered to humans in relatively large quantities, their blood concentration does not increase very much and an influence on amino acid distribution in blood is small. Such findings have increased a demand for highly dense amino acid infusion solutions for administration via the central vein in which a rate of the branched chain amin acids to the total L-amino acids (BCAA/TAA) is increased.

However, solubilities of Leu, Ile and Val in water at 25° C. are 2.19, 4.12 and 8.85 g/dl, respectively. When other amino acids are co-present, any of the solubilities decreases. For example, a mixture of Leu and Ile in almost equimolar amounts has a solubility of approximately 2.2 g/dl and a mixture of Leu, Ile, Val, L-methionine (Met) and Phe has a solubility of approximately 4.5 g/dl. Thus, when it is wished to raise a concentration of the branched chain amino acids, a concentration of other L-amino acids should be extremely reduced so that unbalanced distribution of L-amino acids in blood is caused. Accordingly, its application has been limited to special cases for a patient with hepatic encephalosis, etc. That is, it has been difficult to prepare highly concentrated amino acid infusion solutions containing other L-amino acids in a well-balanced state to be suited for any desired purpose, while increasing a ratio of the branched chain amino acids to the total L-amino acids.

Some proposals have already been made to increase the concentration of the L-amino acid content using water soluble oligopeptides, though the proposals don't pay attention particularly to the branched chain amino acids. For example, in Japanese Patent Application Laid-Open No. 56-140923, there is disclosed a method using at least two oligopeptides containing glycine residue as the N-terminal. According to this method, however, a proportion of the specific amino acid, glycine (Gly), becomes extremely high to cause imblanced distribution of L-amino acids in blood, which is not preferable. Furthermore, in Japanese Patent Application Laid-Open No. 61-247354, there is disclosed a method using oligopeptide(s) containing a glycine residue as the N-terminal in combination with oligopeptide(s) containing as the N-terminal a residue from at least one amino acid selected from the group consisting of Ala, L-arginine (Arg) and L-lysine (Lys). However, as is demonstrated in the Laid-Open Applications, an increased concentration of the branched chain amino acids is accompanied by a high concentration of Gly, Ala, Arg or Lys. As a result, it is difficult to provide sitologically preferred compositions.

The present invention aims at providing highly dense amino acid infusion solutions which can exhibit excellent nutrient effect in various diseases. That is, a third problem to be solved by the present invention is, under the above-described prior art, to provide L-amino acid compositions for infusion in which a rate of the branched chain amino acid components is increased, other amino acids are formulated in a well balanced state and a high concentration can be achieved without any limitation on preparations.

Furthermore, as has been discussed above, as recent studies on amino acid metabolism under morbid conditions have been advanced, it has been desired to develop amino acid infusion solutions used for pathologic conditions such as surgical seizures, hepatic insufficiency, renal disorder, septicemia, premature infant, etc. In particular, attention has been drawn to the branched chain L-amino acids (BCAA) metabolized in organs other than liver and by enhancing a proportion of BCAA to the total L-amino acids (TAA), nutrient effects have been increased in pre-operative and post-operative stages. For treatment of some specific disease, there is known Fischer et al's composition applicable to patients with hepatic encephalosis in which the BCAA content is increased while the contents of Met, Phe and Trp are restricted; or the like.

A ratio of BCAA to be incorporated has also been studied, and, as a result, it has been found that an increased ratio of Leu is necessary for exhibiting good effects on sitological parameters. It is also known by the studies heretofore made that when a ratio of BCAA to TAA (BCAA/TAA) is 25 to 60%, good results are given. In addition, as has been stated above, even though BCAA is intravenously administered in a relatively large dose, its blood concentration does not increase so that imbalanced distribution of L-amino acids in blood does not occur. Based on these research results, it has been demanded to increase the ratio of BCAA to TAA (BCAA/TAA) and increase the concentration of BCAA more. In particular, as the complete intravenous utilizing the central veins has been advanced, an amount of water administered is limited so that a much higher concentration of an infusion solution has been demanded, as has been also stated above. However, solubilities of Leu, Ile and Val in water at 25° C. are 2.19, 4.12 and 8.85 g/dl, respectively. When these amino acids are further mixed with other amino acids, any of the solubilities decreases, as has been already stated. Among them, it is difficult to increase the concentration of Leu, which is sitologically desirable. I.e., there has been a bar against the preparation of dense infusion solutions having a high concentration of BCAA in compliance with the purpose of use.

Several proposals have already been made, as has been stated above, to increase the concentration of the L-amino acid components in general (Japanese Patent Application Laid-Open No. 56-140923 and Japanese Patent Application Laid-Open No. 61-247354). However, as is demonstrated in the Laid-Open Applications, an increased concentration of BCAA is accompanied by an increased concentration of other L-amino acids, and this is not preferred.

As a result of extensive investigations, the present inventors have found that by mixing a composition mainly composed of BCAA with an ordinary amino acid infusion solution in a suitable ratio, an amino acid infusion solution suited for various specific morbid conditions can be readily obtained.

A fourth problem to be solved by the present invention is, under the above-described prior art, to provide BCAA compositions which are used for preparing amino acid infusion solutions which are free from any preparation restrictions but contain BCAA in a large ratio suited for the purpose in a necessary dose by simply adding such BCAA composition to an ordinary amino acid infusion solution when administered.

SUMMARY OF THE INVENTION

The present invention completed to solve the above problems relates, in one of its aspects, to stabilized and-/or dense L-amino acid nutrient compositions in which at least one of some specific L-amino acids is contained partly or substantially completely in the form of oligopeptide(s) containing at least one residue of the same L-amino acid(s).

In a second aspect, the present invention relates to stabilizer-free nutrient infusion compositions and more particularly, to stabilized, amino acid-containing nutrient infusion compositions which are free of any stabilizer conventionally considered to be necessary.

In a third aspect, the present invention relates to a nutrient infusion composition, and more specifically to an amino acid nutrient infusion composition containing a dipeptide of L-tyrosine.

In a fourth aspect, the present invention relates to nutrient infusion compositions, and more particularly to amino acid nutrient infusion compositions which contain a dipeptide of Leu which is a branched chain amino acid.

In a fifth aspect, the present invention relates to novel compositions for amino acid infusion solutions, and more particularly to compositions for amino acid infusion solutions which compositions contain a dipeptide of branched chain L-amino acid(s).

DETAILED DESCRIPTION OF THE PREFERRED EMBODIMENTS

A First Embodiment:

There are known among common infusion solutions which are administered intravenously, glucose solutions, xylitol solutions, electrolyte solutions, lacticic acid-added Ringer solutions and L-amino acid solutions.

Many various compositions have been proposed for amino acid infusion solutions, but there still remain problems to be solved, as has been discussed above.

The present inventors have, as a result of their profound research to solve such problems, found that it is a solution common to the problems to use some specific L-amino acids in the form of their oligopeptide, and completed the present invention on the basis of these findings.

I.e., the present invention gives, in a first embodiment, amino acid infusion solutions and mixtures of L-amino acids which form an amino acid infusion solution when dissolved in water, in which solutions or mixtures at least one of Trp, Tyr, Leu, Ile and Val is partly or substantially completely in the form of oligopeptide(s).

Examples of such oligopeptides and their preparation will be mentioned later.

Amino acid infusion solutions and mixtures of L-amino acids which give an amino acid infusion solution when dissolved in water may be prepared in any conventional ways of preparing amino acid infusion solutions and mixtures of L-amino acids which give an amino acid infusion solution when dissolved in water, except that at least one of the above-mentioned specific amino acids is partly or substantially completely in the form of oligopeptide(s).

A Second Embodiment:

In view of the foregoing findings that the prime cause of the instability of amino acid infusion solutions, the present inventors have made various investigations and have found that by using Trp in the form of dipeptide or tripeptide, instability of amino acid infusion solutions such as coloration, etc. can be prevented and at the same time, can achieve a high concentration of Trp and, have come to accomplish the present invention.

That is, the present invention provides, in a second embodiment, nutrient infusion compositions containing essential L-amino acids characterized by containing Trp in the form of dipeptide or tripeptide containing at least one L-tryptophan residue and being free of any stabilizer.

It is to be noted that substantially all the Trp must be in the form of dipeptide or tripeptide in nutrient infusion compositions of the present invention in order to realize the object.

Examples of the dipeptides and tripeptides used in the present invention include L-tryptophyl-glycine (Trp-Gly), L-tryptophyl-L-alanine (Trp-Ala), L-tryptophyl-L-leucine (Trp-Leu), L-tryptophyl-L-isoleucine (Trp-Ile), L-tryptophyl-L-valine (Trp-Val), L-alanyl-L-tryptophan (Ala-Trp), L-leucyl-L-tryptophan (Leu-Trp), L-isoleucyl-L-tryptophan (Ile-Trp), L-valyl-L-tryptophan (Val-Trp), glycyl-L-tryptophyl-glycine (Gly-Trp- Gly), glycyl-L-tryptophyl-L-alanine (Gly-Trp-Ala), glycyl-L-tryptopyl-L-leucine (Gly-Trp-Leu), L-alanyl-L-tryptophyl-glycine (Ala-Trp-Gly), L-alanyl-L-tryptophyl-L-alanine (Ala-Trp-Ala), L-alanyl-L-tryptophyl-L-leucine (Ala-Trp-Leu). Among these peptides, Trp-Ala and Trp-Leu are the best two in stabilizing activity, as will be seen from the test examples given hereinafter.

The peptides can be prepared by conventional peptide synthesis.

The amino acid composition in the nutrient infusion compositions of the present invention may be a new one suited for a desired purpose or may be any conventional one, supposing that the dipeptide or tripeptide used are converted to the component L-amino acids.

According to the present invention, L-amino acids and oligopeptides may be used either in the free form or in the pharmaceutically acceptable salt forms such as metallic salts, e.g., with sodium and potassium, mineral acid addition salts, e.g, with hydrochloric and sulfuric acids, and organic acid addition salts, e.g., with acetic and lactic acids.

The nutrient infusion compositions of the present invention may also contain nutrients other than amino acids, such as electrolytes, trace elements, etc.

They are not critical in their concentration, and can have concentrations of known amino acid infusion solutions. Their pH can be the same as those of known amino acid infusion solutions, and may usually be in the range of about 4 to about 8. Their pH adjusting agents can be the same ones for known amino acid infusion solutions.

The present invention will be described in more detail by referring to the examples and the test examples below.

EXAMPLE 1

To the amino acid composition shown in Table 1 was added 1.7 g of Trp-Ala. The mixture was dissolved in distilled water for injection by heating to make the whole volume 0.99 liter. After adjusting its pH to about 6.5 with an aqueous acetic acid solution, the whole volume was made 1 liter. The solution was filtered through a membrane filter having a pore diameter of 0.45μ. The filtrate was filled in a 200 ml glass bottle. After replacing the air with nitrogen gas, the bottle was tight-sealed. A nutrient solution for intravenous administration was then prepared by steam sterilization.

The preparation contained 1.3 g/l of Trp and 7.1 g/l of Ala supposing that the dipeptide was converted to the component L-amino acids, i.e., Trp and Ala.

TABLE 1

| Amino Acid Composition (g) | | | | | |
|---|---|---|---|---|---|
| Ile | 9.1 | Val | 14.0 | Glu | 0.5 |
| Leu | 12.9 | Arg | 9.0 | Pro | 5.0 |
| Lys | 7.1 | His | 5.0 | Ser | 1.7 |
| Met | 4.4 | Gly | 7.0 | Tyr | 0.4 |
| Phe | 7.0 | Ala | 6.5 | | |
| Thr | 7.5 | Asp | 1.0 | | |

In the table, Thr, His, Glu, Asp, Pro and Ser represent L-Threonine, L-Histidine, L-Glutamic acid, L-Aspartic acid, L-Proline and L-Serine, respectively.

EXAMPLE 2

To the amino acid composition shown in Table 2 was added 3.4 g of Trp-Ala. Subsequently, the mixture was treated in a manner similar to Example 1 to give an infusion solution.

When the dipeptide was calculated as Trp and Ala, the solution contained 2.5 g/l of Trp and 4.1 g/l of Ala.

TABLE 2

| Amino Acid Composition (g) | | | | | |
|---|---|---|---|---|---|
| Ile | 7.5 | Val | 7.5 | Cys | 0.25 |
| Leu | 10.0 | Arg | 2.0 | Glu | 0.25 |
| Lys | 5.0 | His | 2.5 | Orn | 1.5 |
| Met | 5.0 | Gly | 2.0 | Pro | 2.0 |
| Phe | 5.0 | Ala | 3.0 | Ser | 1.0 |
| Thr | 2.5 | Asp | 0.25 | Tyr | 0.5 |

In the table, Cys and Orn represent L-cystein and L-ornithine respectively.

EXAMPLE 3

To the amino acid composition shown in Table 3 was added 6.7 g of Trp-Ala. Subsequently, the mixture was treated in a manner similar to Example 1 to give an infusion solution.

When the dipeptide was calculated as Trp and Ala, the solution contained 5.0 g/l of Trp and 4.7 g/l of Ala.

TABLE 3

| Amino acid Composition (g) | | | | | |
|---|---|---|---|---|---|
| Ile | 9.1 | Val | 14.0 | Glu | 0.5 |
| Leu | 12.9 | Arg | 9.0 | Pro | 5.0 |
| Lys | 7.1 | His | 5.0 | Ser | 1.7 |
| Met | 4.4 | Gly | 5.1 | Tyr | 0.4 |
| Phe | 7.0 | Ala | 2.5 | | |
| Thr | 7.5 | Asp | 1.0 | | |

EXAMPLES 4 to 7

The amino acids and dipeptides shown in Table 4 were mixed as is indicated under each example, and the mixtures were treated in a manner similar to Example 1 to give infusion solutions.

TABLE 4

| | Amino acid Compositions (g) | | | |
|---|---|---|---|---|
| | Example No. | | | |
| | 4 | 5 | 6 | 7 |
| Ile | 7.2 | 9.1 | 9.1 | 7.5 |
| Leu | 11.3 | 12.9 | 12.9 | 10.0 |
| Lys | 8.1 | 7.0 | 7.1 | 5.0 |
| Met | 11.3 | 4.4 | 4.4 | 5.0 |
| Phe | 11.3 | 7.0 | 7.0 | 5.0 |
| Thr | 5.2 | 5.0 | 7.5 | 2.5 |
| Val | 8.3 | 14.0 | 14.0 | 7.5 |
| Arg | 0 | 9.0 | 9.0 | 2.0 |
| His | 5.7 | 4.0 | 5.0 | 2.5 |
| Gly | 0 | 3.0 | 7.0 | 2.0 |
| Ala | 0 | 0 | 6.5 | 2.0 |
| Asp | 0 | 1.0 | 1.0 | 0.25 |
| Cys | 0 | 0 | 0.5 | 0.25 |
| Glu | 0 | 0.5 | 0.5 | 0.25 |
| Pro | 0 | 4.0 | 5.0 | 2.0 |
| Ser | 0 | 1.7 | 1.7 | 1.0 |
| Tyr | 0 | 0.4 | 0.4 | 0.5 |
| Orn | 0 | 0 | 0 | 0.5 |
| Trp—Ala | 3.6 | 20.1 | 0 | 0 |
| Ala—Trp | 0 | 0 | 1.7 | 3.4 |

TEST EXAMPLE 1

With respect to 0.5% aqueous solution of each of the representative dipeptides, tripeptides and Trp, transmittance after sterilization (105° C., 60 minutes) was measured. The results are shown in Table 5.

In addition, solubility in water was determined. The results are shown in Table 6.

It is noted that any peptide is extremely stable as compared to Trp and its solubility is improved.

TABLE 5

| Transmittance after Sterilization (T %, 430 nm) | |
|---|---|
| Trp | 90.7 |
| Trp—Gly | 98.5 |
| Trp—Ala | 99.3 |
| Trp—Leu | 99.2 |
| Ala—Trp | 98.1 |
| Gly—Trp—Gly | 99.2 |
| Gly—Trp—Ala | 99.1 |

TABLE 6

| Solubility in Water (g/dl) | |
|---|---|
| Trp | 1.14 |
| Trp—Gly | 3.29 |
| Trp—Ala | 5.20 |
| Trp—Leu | 3.50 |
| Ala—Trp | 5.00 |

TEST EXAMPLE 2

With respect to the infusion solutions obtained in Examples 1 to 4 and Comparative Examples 1 to 8, transmittance before and after sterilization (105° C., 80 minutes) was measured, respectively. The results are shown in Tables 7 to 10.

TABLE 7

| | Transmittance (T %, 430 nm) | | |
|---|---|---|---|
| | Before Sterilization | After Sterilization | Difference in Transmittance |
| Example 1 | 99.2 | 98.9 | 0.3 |
| Comparative Example 1 | 99.3 | 97.5 | 1.8 |
| Comparative Example 2 | 99.2 | 99.0 | 0.2 |

COMPARATIVE EXAMPLE 1

An infusion solution was prepared by following Example 1 except that Trp and Ala were used instead of Trp-Ala.

COMPARATIVE EXAMPLE 2

An infusion solution was prepared by following comparative Example 1 except that 0.5 g/l of sodium hydrogensulfite was additionally added.

TABLE 8

| | Transmittance (T %, 430 nm) | | |
|---|---|---|---|
| | Before Sterilization | After Sterilization | Difference in Transmittance |
| Example 2 | 99.6 | 99.2 | 0.4 |
| Comparative Example 3 | 99.7 | 98.3 | 1.6 |
| Comparative Example 4 | 99.8 | 99.5 | 0.4 |

COMPARATIVE EXAMPLE 3

An infusion solution was prepared by following Example 2 except that Trp and Ala were used instead of Trp-Ala.

COMPARATIVE EXAMPLE 4

An infusion solution was prepared by following Comparative Example 3 except that 0.5 g/l of sodium hydrogensulfite was additionally added.

TABLE 9

| | Transmittance (T %, 430 nm) | | |
|---|---|---|---|
| | Before Sterilization | After Sterilization | Difference in Transmittance |
| Example 3 | 98.9 | 98.5 | 0.4 |
| Comparative Example 5 | 98.9 | 95.2 | 3.7 |
| Comparative Example 6 | 98.9 | 98.5 | 0.4 |

COMPARATIVE EXAMPLE 5

An infusion solution was prepared by following Example 3 except that Trp and Ala were used instead of Trp-Ala.

COMPARATIVE EXAMPLE 6

An infusion solution was prepared by following Comparative Example 5 except that 0.5 g/l of sodium hydrogensulfite was additionally added.

TABLE 10

| | Transmittance (T %, 430 nm) | | |
|---|---|---|---|
| | Before Sterilization | After Sterilization | Difference in Transmittance |
| Example 4 | 99.6 | 99.3 | 0.3 |
| Comparative Example 7 | 99.7 | 98.4 | 1.3 |
| Comparative Example 8 | 99.7 | 99.4 | 0.3 |

COMPARATIVE EXAMPLE 7

An infusion solution was prepared by following Example 4 except that Trp and Ala were used instead of Trp-Ala.

COMPARATIVE EXAMPLE 8

An infusion solution was prepared by following Comparative Example 7 except that 0.5 g/l of sodium hydrogensulfite was additionally added.

As described above, it is understood that the compositions of the present invention provide high stability equivalent to the compositions in which sodium hydrogensulfite was incorporated.

According to the present invention, as is evident from the foregoing examples and test examples, amino acid nutrient infusion compositions which are sufficiently stable can be provided without using stabilizers such as hydrogensulfites or sulfites harmful to the body. Furthermore, the Trp component can be contained in higher concentrations if necessary and desired, and infusion solutions having new formulations which are suited for various purposes can be provided.

The dipeptide and tripeptide used in accordance with the present invention are stable in an aqueous solution and are not colored even after sterilization by heating. Furthermore, solubility in water is also improved.

In fact, the amino acid nutrient infusion compositions of the present invention containing Trp in the form of dipeptide or tripeptide is not colored without containing any stabilizer therein but is sufficiently stable from an aspect of medical preparations.

The dipeptide or tripeptide used in accordance with the present invention is effectively utilized in the living body.

A Third Embodiment:

The present inventors have been studying in order to solve the second problem and, as a result, have discovered that the solubility of Tyr which is a Pharmaceutical problem may be solved by using a dipeptide of Tyr and that in order to further obtain the effect of Tyr, the concentration of Tyr in an amino acid infusion solution has an optimum range and that the optimum range is related to the concentrations of the other L-amino acids incorporated at the same time, and have accomplished the present invention on these findings.

As has been described before, Tyr has been found to be an essential amino acid for certain sick conditions, and the necessity of a high concentration has been urged for practical purposes. However, owing to the pharmaceutical problems, comprehensive studies on the correlation of Tyr with other L-amino acids and concentrations thereof have not yet been done, and thus the formulations to realize its higher concentrations have not been yet determined. Tyr is synthesized from its precursor essential amino acid Phe, and Phe is the most correlated amino acid.

Based on such consideration, the present inventors had thought that there must be a particular correlation between the amounts of Tyr and Phe incorporated and the amounts of essential L-amino acids and non-essential L-amino acids incorporated, and have continued the study. As a result, they have discovered an amino acid composition ratio which may be used for morbid conditions such as liver diseases, uremia etc. as well as for immature infants, newborn infants etc., and have accomplished the present invention.

Accordingly, the present invention provides, in a third embodiment, an amino acid nutrient infusion composition containing essential amino acids, non-essential L-amino acids and at least one dipeptide containing at lest one L-tyrosine residue, which is characterized by that when said dipeptide is calculated as the respective component L-amino acids, at least the respective amino acids indicated in Table 11 are contained in the respective ranges indicated therein, that the weight ratio of Tyr to Phe (Tyr/Phe) is 0.1 or more and that the concentration of Tyr is 0.6 g/l or more.

TABLE 11

| Amino Acid | Composition Range (g/100 g-Total Amino Acids) |
| --- | --- |
| Ile | 5.0–20.0 |
| Leu | 5.0–20.0 |
| Lys | 3.0–15.0 |
| Met | 1.0–10.0 |
| Phe | 1.0–10.0 |
| The | 2.0–12.0 |
| Trp | 0.25–5.0 |
| Val | 5.0–20.0 |
| Ala | 2.0–15.0 |
| Arg | 2.0–15.0 |
| Asp | 0–4.0 |
| Cys | 0–2.0 |
| Glu | 0–8.0 |
| His | 0–10.0 |
| Pro | 0–10.0 |
| Ser | 0–8.0 |
| Tyr | 0.5–10.0 |
| Gly | 3.0–15.0 |
| Orn | 0–5.0 |
| Tau | 0–15.0 |

The above-described "when said dipeptide is calculated as the respective component L-amino acids" means that "when the amount of said dipeptide is calculated as the amounts of the respective L-amino acids formed when fully hydrolyzed".

As dipeptides containing at least one L-tyrosine residue used in the present invention, there may be preferably used L-threonyl-L-tyrosine (Thr-Tyr), L-leucyl-L-tyrosine (Leu-Tyr), L-isoleucyl-L-tyrosine (Ile-Tyr), L-valyl-L-tyrosine (Val-Tyr), L-tyrosyl-glycine (Tyr-Gly), L-tyrosyl-L-alanine (Tyr-Ala), L-tyrosyl-L-leucine (Tyr-Leu), L-tyrosyl-L-isoleucine (Tyr-Ile), L-tyrosyl-L-valine (Tyr-Val), L-tyrosyl-L-aspartic acid (Tyr-Asp), L-tyrosyl-L-lysine (Tyr-Lys), L-tyrosyl-L-threonine (Tyr-Thr), L-tyrosyl-L-glutamic acid (Tyr-Glu) and L-tyrosyl-L-glutamine (Tyr-Gln).

These peptides can be prepared by conventional peptide synthesis.

By incorporating at least one dipeptide containing at least one L-tyrosine residue, an amino acid nutrient infusion composition containing Tyr at a high concentration is presented.

Further, the amino acids and dipeptides according to the present invention may be used not only as free acid forms but also as pharmaceutically acceptable salts, for example, metal salts such as sodium salts, potassium salts etc., mineral acid salts such as hydrochlorides, sulfates etc. or organic acid salts such as acetates, lactates etc. Further, the amino acids other than those made into the dipeptides may also be used as pharmaceutically acceptable N-acyl derivatives, ester derivatives or oligopeptides. Furthermore, when they are made into amino acid infusion compositions, such composition may be produced in the conventional manner by using conventionally employed stabilizers, pH modifiers etc.

An effective dosage of the total amino acids of the present invention is 60 - 90 g/day for adults.

The present invention will be more specifically described by the examples and test examples given below.

EXAMPLE 8

8.6 g of Tyr-Ala was added to the amino acid composition set forth in Table 12, dissolved in injectable distilled water by heating, and then the total amount was adjusted to 0.99 l. Thereafter, the pH was adjusted to 6.0–7.0 with an acetic acid solution or other organic acid solution (lactic acid, malic acid, citric acid etc.), and the total amount was adjusted to 1 liter. This aqueous solution was filtered through a membrane filter having a pore diameter of 0.45 μ, filled into a 200 ml glass vial, followed by nitrogen replacement and tight-sealing. This was sterilized by steam at high pressure to prepare an infusion solution for intravenous administration.

This preparation contained Ala and Tyr at 3.0 g/l and 6.2 g/l, respectively, if the dipeptide was calculated as the respective component L-amino acids,

TABLE 12

| Amounts of Amino Acids Incorporated (g/l) | | | | | |
| --- | --- | --- | --- | --- | --- |
| Ile | 9.0 | Val | 10.0 | Pro | 5.0 |
| Leu | 13.0 | Ala | 6.0 | Ser | 3.0 |
| Lys | 10.0 | Arg | 10.0 | Gly | 5.0 |
| Met | 2.5 | Asp | 2.0 | Tau | 3.5 |
| Phe | 3.0 | Cys | 1.0 | | |
| Thr | 5.0 | Glu | 2.0 | | |
| Trp | 2.5 | His | 5.0 | | |

EXAMPLE 9

7.2 g of Leu-Tyr was added to the amino acid composition set forth in Table 13, and thereafter by procedures similar to those described in Example 8, an infusion solution for intravenous administration was prepared.

This preparation contained Leu and Tyr at 3.2 g/l and 4.4 g/l, respectively, if the dipeptide was calculated as the respective component L-amino acids.

TABLE 13

| Amounts of Amino acids Incorporated (g/l) | | | | | |
|---|---|---|---|---|---|
| Ile | 8.5 | Val | 10.0 | Pro | 6.0 |
| Leu | 12.6 | Ala | 12.0 | Ser | 3.0 |
| Lys | 12.0 | Arg | 9.0 | Gly | 10.0 |
| Met | 7.5 | Asp | 2.0 | Tau | 7.5 |
| Phe | 3.0 | Cy | 1.0 | | |
| Thr | 8.0 | Glu | 2.0 | | |
| Trp | 2.5 | His | 5.0 | | |

EXAMPLE 10

11.8 g of Val-Tyr was added to the amino acid composition set forth in Table 14, and thereafter by procedures similar to those described in Example 8, an infusion solution for intravenous administration was prepared.

This preparation contained the Val and Tyr at 4.9 g/l and 7.6 g/l, respectively, if dipeptide was calculated as the respective component L-amino acids.

TABLE 14

| Amounts of Amino acids Incorporated (g/l) | | | | | |
|---|---|---|---|---|---|
| Ile | 7.0 | Val | 2.1 | Pro | 4.6 |
| Leu | 14.0 | Ala | 8.3 | Ser | 2.1 |
| Lys | 6.9 | Arg | 9.0 | Gly | 10.5 |
| Met | 5.7 | Asp | 3.0 | | |
| Phe | 3.0 | Cys | 1.0 | | |
| Thr | 6.3 | Glu | 3.5 | | |
| Trp | 1.1 | His | 6.0 | | |

EXAMPLES 11–20

The amino acid compositions and peptides set forth in Tables 15 and 15a were formulated, and thereafter by procedures similar to those described in Example 8, infusion solution for intravenous administration were prepared.

TABLE 15

| Amino Acids and Dipeptides | Amounts of Amino Acids and Dipeptides Incorporated (g/l) — Example No. | | | | |
|---|---|---|---|---|---|
| | 11 | 12 | 13 | 14 | 15 |
| Ile | 7.5 | 7.0 | 7.5 | 10.0 | 7.3 |
| Leu | 13.0 | 14.0 | 12.8 | 12.0 | 14.2 |
| Lys | 9.1 | 9.5 | 10.0 | 8.0 | 9.5 |
| Met | 4.4 | 3.9 | 2.5 | 2.5 | 2.0 |
| Phe | 4.2 | 3.0 | 2.0 | 3.0 | 3.0 |
| Thr | 7.5 | 5.7 | 5.0 | 5.0 | 6.2 |
| Trp | 1.3 | 2.0 | 2.5 | 2.5 | 2.0 |
| Val | 8.0 | 7.0 | 12.0 | 6.5 | 7.5 |
| Ala | 7.1 | 7.0 | 6.0 | 6.0 | 5.9 |
| Arg | 9.0 | 10.5 | 10.0 | 10.0 | 7.0 |
| Asp | 1.1 | 1.0 | 2.0 | 2.0 | 2.0 |
| Cys | 0 | 1.0 | 1.0 | 1.0 | 0.5 |
| Glu | 0.5 | 1.4 | 2.0 | 2.0 | 4.5 |
| His | 5.0 | 5.0 | 5.0 | 4.0 | 4.1 |
| Pro | 5.0 | 5.0 | 5.0 | 3.0 | 4.5 |
| Ser | 1.7 | 3.0 | 3.0 | 2.5 | 3.0 |
| Gly | 6.5 | 5.9 | 5.0 | 6.0 | 7.5 |
| Orn | 0 | 0 | 1.0 | 1.5 | 0 |
| Tau | 0 | 0 | 3.2 | 0 | 3.5 |
| Leu—Tyr | 0 | 0 | 7.2 | 0 | 0 |
| Ile—Tyr | 0 | 3.4 | 0 | 0 | 0 |
| Val—Tyr | 0 | 0 | 0 | 10.8 | 0 |
| Tyr—Gly | 1.7 | 0 | 0 | 0 | 0 |
| Tyr—Ala | 0 | 0 | 0 | 0 | 5.4 |
| Tyr Amount | 1.3 | 2.1 | 4.4 | 7.0 | 3.9 |
| Amount of the other Amino Acid in the peptide | Gly 0.5 | Ile 1.5 | Leu 3.2 | Val 4.5 | Ala 1.9 |

TABLE 15a

| Amino Acids and Dipeptides | Amounts of Amino Acids and Dipeptides Incorporated (g/l) — Example No. | | | | |
|---|---|---|---|---|---|
| | 16 | 17 | 18 | 19 | 20 |
| Ile | 8.0 | 9.0 | 8.5 | 9.1 | 5.6 |
| Leu | 14.0 | 13.0 | 13.0 | 13.1 | 12.5 |
| Lys | 9.5 | 10.0 | 12.0 | 8.1 | 9.3 |
| Met | 3.9 | 2.5 | 7.5 | 4.4 | 3.5 |
| Phe | 4.0 | 5.1 | 1.7 | 4.5 | 3.3 |
| Thr | 6.7 | 8.0 | 10.8 | 8.5 | 6.5 |
| Trp | 2.0 | 2.5 | 2.2 | 1.3 | 1.3 |
| Val | 8.0 | 11.0 | 7.4 | 9.0 | 4.5 |
| Ala | 5.5 | 2.5 | 12.0 | 6.0 | 3.1 |
| Arg | 10.5 | 8.8 | 10.3 | 9.0 | 8.9 |
| Asp | 1.0 | 3.0 | 1.7 | 2.7 | 3.4 |
| Cys | 1.0 | 1.0 | 0 | 0 | 1.0 |
| Glu | 1.0 | 2.0 | 0.9 | 4.5 | 6.5 |
| His | 4.4 | 5.0 | 8.5 | 5.0 | 6.0 |
| Pro | 5.0 | 5.0 | 8.5 | 5.0 | 3.3 |
| Ser | 3.0 | 2.5 | 2.9 | 1.7 | 2.2 |
| Gly | 7.0 | 5.0 | 13.5 | 7.0 | 9.7 |
| Orn | 0 | 0 | 0 | 0 | 0 |
| Tau | 0 | 2.5 | 5.5 | 0 | 0 |
| Leu—Tyr | 0 | 0 | 0 | 1.0 | 0 |
| Ile—Tyr | 0 | 0 | 0 | 0 | 0 |
| Val—Tyr | 0 | 0 | 6.2 | 0 | 0 |
| Tyr—Gly | 1.5 | 0 | 0 | 0 | 0 |
| Tyr—Ala | 0 | 7.1 | 0 | 0 | 8.8 |
| Tyr Amount | 1.1 | 5.1 | 4.0 | 0.6 | 6.3 |
| Amount of the other Amino Acid in the peptide | Gly 0.5 | Ala 2.5 | Val 2.6 | Leu 0.5 | Ala 3.1 |

TEST EXAMPLE 3

An SD strain male rat of a body weight of about 170 g was planted with a silicone rubber catheter in the right upper great vein under anesthetized condition, and immediately subjected to transfusion application by an intravenous hyperalimentation therapy for a week (total calorie: 332 Kcal/Kg/day, nitrogen: 1.83 gN/Kg/day). The three applied nutrient infusion solutions had the same composition of sugars, electrolytes, vitamins and trace elements but different amino acid compositions.

The infusion solution tested was that of Example 8, and as comparison infusion solutions, Infusion Solutions I and II formulated as in Table 16 were used.

The study on the effects were conducted by examining the change in body weight and the nitrogen balance. As a result, it is observed that the infusion solution of Example 8 gave a remarkable improvement as compared with the comparison infusion solution as shown in Table 17.

TABLE 16

Amino Acid Compositions of Infusion Solution I and II

| Amino Acids | Infusion Solution I (g/l) | Infusion Solution II (g/l) |
|---|---|---|
| Ile | 9.0 | 9.0 |
| Leu | 13.0 | 13.0 |
| Lys | 10.0 | 10.0 |
| Met | 2.5 | 2.5 |
| Phe | 3.0 | 8.7 |
| Thr | 5.0 | 5.0 |
| Trp | 2.5 | 2.5 |
| Val | 10.0 | 10.0 |
| Ala | 9.0 | 9.0 |
| Arg | 10.0 | 10.0 |
| Asp | 2.0 | 2.0 |
| Cys | 1.0 | 1.0 |
| Glu | 2.0 | 2.0 |
| His | 5.0 | 2.0 |
| Pro | 5.0 | 5.0 |
| Ser | 3.0 | 5.0 |
| Tyr | 0.4 | 0.4 |
| Gly | 7.6 | 5.0 |
| Tau | 3.5 | 3.5 |

TABLE 17

Nutrient Effect of the Example 8 Infusion Solution

| Amino Acid Infusion Solution | Gain in Body Weight (g/7 days) | Nitrogen Balance (g/7 days) |
|---|---|---|
| Solution I | 11.0 | 1.0 |
| Solution II | 22.1 | 1.5 |
| Solution of Example 8 | 28.3 | 1.7 |

TEST EXAMPLES 4-7

Using the infusion solutions of Examples 9, 10, 13 and 20 and the comparison infusion solutions set forth in Table 18 and 18a, procedures similar to those in Test Example 3 were conducted. The results are shown in Table 19.

TABLE 18

Compositions of Comparison Infusion Solutions

| Amino Acids and Dipeptides | Test Example 4 Comparison Infusion Solution for Example 9 | | Test Example 5 Comparison Infusion Solution for Example 10 | |
|---|---|---|---|---|
| | III | IV | V | VI |
| Ile | 8.5 | 8.5 | 7.0 | 7.0 |
| Leu | 15.8 | 15.8 | 14.0 | 14.0 |
| Lys | 12.0 | 12.0 | 6.9 | 6.9 |
| Met | 7.5 | 7.5 | 5.7 | 5.7 |
| Phe | 3.0 | 7.0 | 3.0 | 9.9 |
| Thr | 8.0 | 8.0 | 6.3 | 6.3 |
| Trp | 2.5 | 2.5 | 1.1 | 1.1 |
| Val | 10.0 | 10.0 | 7.0 | 7.0 |
| Ala | 12.0 | 12.0 | 8.3 | 8.3 |
| Arg | 9.0 | 9.0 | 9.0 | 9.0 |
| Asp | 2.0 | 2.0 | 3.0 | 3.0 |
| Cys | 1.0 | 1.0 | 1.0 | 1.0 |
| Glu | 2.0 | 2.0 | 3.5 | 3.5 |

TABLE 18-continued

Compositions of Comparison Infusion Solutions

| Amino Acids and Dipeptides | Test Example 4 Comparison Infusion Solution for Example 9 | | Test Example 5 Comparison Infusion Solution for Example 10 | |
|---|---|---|---|---|
| | III | IV | V | VI |
| His | 5.0 | 5.0 | 6.0 | 6.0 |
| Pro | 6.0 | 6.0 | 4.6 | 4.6 |
| Ser | 3.0 | 3.0 | 2.1 | 2.1 |
| Tyr | 0.4 | 0.4 | 0.4 | 0.4 |
| Gly | 11.8 | 10.0 | 13.6 | 10.5 |
| Orn | 0 | 0 | 0 | 0 |
| Tau | 7.5 | 7.5 | 0 | 0 |

TABLE 18a

Compositions of Comparison Infusion Solutions

| Amino Acids and Dipeptides | Test Example 6 Comparison Infusion Solution for Example 13 | | Test Example 7 Comparison Infusion Solution for Example 20 | |
|---|---|---|---|---|
| | VII | VIII | IX | X |
| Ile | 7.5 | 7.5 | 5.6 | 5.6 |
| Leu | 16.0 | 16.0 | 12.5 | 12.5 |
| Lys | 10.0 | 10.0 | 9.3 | 9.3 |
| Met | 2.5 | 2.5 | 3.5 | 3.5 |
| Phe | 2.0 | 6.0 | 3.3 | 9.0 |
| Thr | 5.0 | 5.0 | 6.5 | 6.5 |
| Trp | 2.5 | 2.5 | 1.3 | 1.3 |
| Val | 12.0 | 12.0 | 4.5 | 4.5 |
| Ala | 6.0 | 6.0 | 6.2 | 6.2 |
| Arg | 10.0 | 10.0 | 8.9 | 8.9 |
| Asp | 2.0 | 2.0 | 3.4 | 3.4 |
| Cys | 1.0 | 1.0 | 1.0 | 1.0 |
| Glu | 2.0 | 2.0 | 6.5 | 6.5 |
| His | 5.0 | 5.0 | 6.0 | 6.0 |
| Pro | 5.0 | 5.0 | 3.3 | 3.3 |
| Ser | 3.0 | 3.0 | 2.2 | 2.2 |
| Tyr | 0.4 | 0.4 | 0.4 | 0.4 |
| Gly | 7.4 | 5.0 | 12.3 | 9.7 |
| Orn | 1.0 | 1.0 | 0 | 0 |
| Tau | 3.2 | 3.2 | 0 | 0 |

TABLE 19

Nutrient Effects of the Examples 9-12 Infusion Solution

| Test Example | Amino Acid Infusion Solution | Gain in Body Weight (g/7 days) | Nitrogen Balance (g/7 days) |
|---|---|---|---|
| 4 | Infusion Solution III | 12.5 | 1.0 |
| | Infusion Solution IV | 24.8 | 1.7 |
| | Infusion Solution of Example 9 | 29.3 | 2.0 |
| 5 | Infusion Solution V | 15.9 | 1.5 |
| | Infusion Solution VI | 27.3 | 1.8 |
| | Infusion Solution of Example 10 | 30.3 | 2.0 |
| 6 | Infusion Solution VII | 13.8 | 1.3 |
| | Infusion Solution VIII | 18.7 | 1.8 |
| | Infusion Solution of | 23.4 | 1.8 |

TABLE 19-continued

Nutrient Effects of the Examples 9-12 Infusion Solution

| Test Example | Amino Acid Infusion Solution | Gain in Body Weight (g/7 days) | Nitrogen Balance (g/7 days) |
|---|---|---|---|
| 7 | Example 13 Infusion Solution IX | 13.0 | 1.2 |
|  | Infusion Solution X | 23.3 | 1.6 |
|  | Infusion Solution of Example 20 | 25.9 | 1.9 |

TEST EXAMPLE 8

Using an SD strain male rat of a body weight of about 170 g, the cortex part of one of the kidneys was surgically enucleated under anesthetized condition, and two weeks later, the other kidney was enucleated. Two weeks after the enucleation of the kidney, the urea nitrogen in blood and the creatinine level were measured, and that having concentrations of 60 mg/dl or higher and 1.4 mg/dl or higher, respectively, was taken as a model attacked by a kidney disease. This rat was planted with a silicone rubber catheter in the right upper great vein, and the infusion maintenance was conducted by an intravenous hyperalimentation therapy for a week (total calorie: 319 Kcal/Kg/day, nitrogen: 0.982 gN/Kg/day). The applied nutrient infusion solutions had the same composition of sugars, electrolytes, vitamins and trace elements but different amino acid compositions. The infusion solution tested was that of Example 8 and Comparison Infusion Solutions I and II shown in Table 16 were used for comparison.

As a result, as shown in Table 20, it was possible to confirm that the infusion solution of Example 8 exerted a remarkable improvement in the change in weight and the nitrogen balance.

TABLE 20

Nutrient Effect of the Example 8 Infusion Solution

| Amino Acid Infusion Solution | Gain in Body Weight (g/7 days) | Nitrogen Balance (g/7 days) |
|---|---|---|
| Comparison Infusion Solution I | 8.3 | 0.84 |
| Comparison Infusion Solution II | 10.0 | 0.95 |
| Infusion Solution of Example 8 | 13.1 | 1.3 |

TEST EXAMPLES 9-12

Using the infusion solutions of Examples 9, 10, 13 and 20 and the comparison infusion solutions set forth in Table 18 and 18a, procedures similar to those in Test Example 8 were conducted. The results are shown in Table 21.

TABLE 21

Nutrient Effects of the Examples 9, 10, 13 and 20 Infusion Solution

| Test Example | Amino Acid Infusion Solution | Gain in Body Weight (g/7 days) | Nitrogen Balance (g/7 days) |
|---|---|---|---|
| 9 | Infusion of Example 9 | 13.5 | 1.5 |
|  | Comparison Infusion Solution III | 8.4 | 1.0 |
|  | Comparison Infusion Solution IV | 8.7 | 1.1 |
| 10 | Infusion Solution of Example 10 | 14.1 | 1.4 |
|  | Comparison Infusion Solution V | 9.1 | 0.95 |
|  | Comparison Infusion Solution VI | 9.2 | 1.1 |
| 11 | Infusion Solution of Example 13 | 14.5 | 1.3 |
|  | Comparison Infusion Solution VII | 9.6 | 1.0 |
|  | Comparison Infusion Solution VIII | 9.3 | 1.1 |
| 12 | Infusion Solution of Example 20 | 15.3 | 1.6 |
|  | Comparison Infusion Solution IX | 9.2 | 1.2 |
|  | Comparison Infusion Solution X | 8.9 | 1.1 |

The present invention relates to an amino acid composition incorporating a dipeptide of L-tyrosine which exerts an excellent nutrient effect on various diseases, and can provide, as is evident from the foregoing examples and test examples, amino acid infusion solutions containing Tyr at high concentrations without suffering from pharmaceutical restrictions in their preparation.

In other words, since Tyr is used as its dipeptide, it was possible to formulate at a concentration suited for the purpose without suffering from the pharmaceutical restrictions.

The formulation of the invention, that is, the nutrient infusion composition can exert excellent nutrient effects on various diseases as an amino acid infusion solution according to the respective sick conditions or as an amino acid infusion solution having high general-purpose utility.

The dipeptides used according to the present invention ar effectively utilized to the living body.

· A Fourth Embodiment:

In order to solve the third problem described above, the present inventors have made various investigations on new components of infusion solutions and, as a result, have found that the problem can be solved by using dipeptide containing an L-leucine residue. The present invention has thus been accomplished.

That is, the present invention provides, in a fourth embodiment, a nutrient infusion composition containing essential amino acids, non-essential L-amino acids and at least one dipeptide whose molecules contain at least one L-leucine residue, which composition is characterized in that said composition contains, if said dipeptide is converted to the respective component L-amino acids, at least the respective amino acids indicated in Table 22 below in the respective composition ranges indicated therein, that the weight ratio of the total branched chain L-amino acids to the total L-amino acids is 0.3–0.6, that the weight ratio of the total essential amino acids to the total non-essential amino acids is 0.9–1.8, and that the weight ratio of Leu, Ile and Val is 1.6–2.4 : 0.8–1.2 : 0.8–1.2.

TABLE 22

| Amino Acid | Composition Range (g/100 g of total amino acids) |
|---|---|
| Ile | 7.0–30.0 |
| Leu | 15.0–45.0 |
| Lys | 5.0–12.0 |
| Met | 2.0–10.0 |
| Phe | 4.0–10.0 |
| Thr | 4.0–9.0 |
| Trp | 1.0–5.0 |
| Val | 7.0–30.0 |
| Arg | 5.0–11.0 |
| His | 3.0–6.0 |
| Gly | 1.0–7.5 |
| Ala | 1.0–8.2 |
| Cys | 0–1.5 |
| Asp | 1.0–4.9 |
| Glu | 0.5–7.0 |
| Pro | 1.0–6.0 |
| Ser | 1.0–3.9 |
| Tyr | 0.1–1.5 |
| Tan | 0–15.0 |

The term "if said dipeptide is converted to the respective L-amino acids" described above means that "if an amount of said dipeptide is calculated as the amounts of the respective L-amino acids formed when the said dipeptide is fully hydrolyzed".

The amino acid composition shown in Table 22 was determined from the view point of sitology and preparation of the nutrient infusion composition.

All the Leu content in the infusion composition doesn't need to be in the form of dipeptide(s) whose molecules contain at least one L-leucine residue. The dipeptide in an amount of more than about 4% of all the Leu content would suffice from the view point of solubility.

Examples of the dipeptides containing at least one L-leucine residue per molecule which can be preferably used in the present invention include L-leucyl-L-isoleucine (Leu-Ile), L-leucyl-L-valine (Leu-Val), L-isoleucyl-L-leucine (Ile-Leu), L-valyl-L-leucine (Val-Leu), etc.

These peptides can be prepared by conventional peptide synthesis.

The amino acids and dipeptides in accordance with the present invention may be used in their free form or in the form of pharmacologically acceptable salts, for example, salts with metals such as sodium and potassium, salts with mineral acids such as hydrochloric acid and sulfuric acid, and salts with organic acids such as acetic acid and lactic acid. Further the L-amino acids other than those in the dipeptide form may also be used as pharmacologically acceptable N-acyl derivatives or ester derivatives or oligopeptides.

Furthermore, when an L-amino acid composition is formed into preparations of the present invention, i.e., nutrient infusion compositions, these preparations may be prepared in a conventional manner, using stabilizers, pH regulators, etc. ordinarily used for amino acid infusion solutions. Their pHs can be the same as those of known amino acid infusion solutions, and may usually be in the range of about 4 to about 8.

The nutrient infusion compositions of the present invention may also contain nutrients other than L-amino acids, such as electrolytes, trace elements, vitamins, minerals, sugars, xylitol.

They are not critical in their concentration, and can have concentrations of known amino acid infusion solutions.

An effective dosage of the total amino acids of the present invention is 60–90 g/day for adults.

The present invention is described in more detail by referring to the examples and test examples below.

EXAMPLE 21

To the amino acid composition shown in Table 23 was added 22.4 g of Leu-Ile. The mixture was dissolved in distilled water for injection by heating to make the whole volume 0.99 liter. After adjusting its pH to 6.0–7.0 with an aqueous acetic acid solution, the whole volume was made 1 liter. The solution was filtered through a membrane filter having a pore diameter of 0.45 μ. The filtrate was filled in a 200 ml glass bottle. After replacing the air with nitrogen gas, the bottle was tight-sealed. A nutrient solution for intravenous administration was then prepared by steam sterilization under high pressure.

TABLE 23

| Amounts of Amino Acids Formulated (g/l) | | | | | |
|---|---|---|---|---|---|
| Ile | 0 | Val | 16.0 | Pro | 5.0 |
| Leu | 8.0 | Ala | 6.0 | Ser | 3.0 |
| Lys | 10.0 | Arg | 10.0 | Tyr | 0.5 |
| Met | 2.5 | Asp | 2.0 | Gly | 5.0 |
| Phe | 5.0 | Cys | 1.0 | Tau | 3.5 |
| Thr | 5.0 | Glu | 2.0 | | |
| Trp | 2.5 | His | 5.0 | | |

The preparation contained 12 g/l of Ile and 20 g/l of Leu if the dipeptide was converted to the respective L-amino acid components. The weight ratio of the total essential amino acids to the total non-essential amino acids (E/N) was 1.7, the ratio of the total branched chain amino acids to the total amino acids (BCAA/TAA) was 0.41, and the Ile : Leu : Val ratio was 1 : 1.7 : 1.3.

EXAMPLE 22

To the amino acid composition shown in Table 24 was added 37.3 g of Ile-Leu. Subsequently, the mixture was treated in a similar manner as in Example 21 to give an infusion solution for intravenous administration.

TABLE 24

| Amounts of Amino Acids Formulated (g/l) | | | | | |
|---|---|---|---|---|---|
| Ile | 0 | Val | 20.0 | Pro | 9.0 |
| Leu | 20.0 | Ala | 12.0 | Ser | 3.0 |
| Lys | 12.0 | Arg | 14.0 | Tyr | 0.5 |
| Met | 7.5 | Asp | 2.0 | Gly | 13.0 |
| Phe | 12.0 | Cys | 1.0 | Tau | 7.5 |
| Thr | 13.0 | Glu | 2.0 | | |
| Trp | 2.5 | His | 9.0 | | |

The preparation contained 20 g/l of Ile and 40 g/l of Leu if the dipeptide was converted to the respective L-amino acid components. The E/N was 1.74, BCAA/TAA was 0.4, and the Ile : Leu : Val ratio was 1 : 2 : 1.

EXAMPLES 23-28

The amino acids and dipeptides shown in Table 25 were mixed and the mixtures were treated in a similar manner as in Example 21 to give infusion solutions for intravenous administration.

TABLE 25

| Amino Acids and Dipeptides | Amounts of Amino Acids and Dipeptides Formulated (g/l) Example No. | | | | | |
|---|---|---|---|---|---|---|
| | 23 | 24 | 25 | 26 | 27 | 28 |
| Ile | 0 | 0 | 12.0 | 20.0 | 9.0 | 8.0 |
| Leu | 9.0 | 8.0 | 2.1 | 17.6 | 7.9 | 7.0 |
| Lys | 7.1 | 9.5 | 10.0 | 12.0 | 7.1 | 9.5 |
| Met | 4.4 | 3.9 | 2.5 | 7.5 | 4.4 | 3.9 |
| Phe | 7.0 | 7.0 | 5.0 | 12.0 | 7.0 | 7.0 |
| Thr | 7.5 | 5.7 | 5.0 | 13.0 | 7.5 | 5.7 |
| Trp | 1.3 | 2.0 | 2.5 | 2.5 | 1.3 | 2.0 |
| Val | 9.0 | 8.0 | 0 | 0 | 0 | 0 |
| Ala | 7.1 | 7.0 | 6.0 | 12.0 | 7.1 | 7.0 |
| Arg | 9.0 | 10.5 | 10.0 | 14.0 | 9.0 | 10.5 |
| Asp | 1.0 | 1.0 | 2.0 | 2.0 | 1.0 | 1.0 |
| Cys | 0 | 1.0 | 1.0 | 1.0 | 0 | 1.0 |
| Glu | 0.5 | 1.0 | 2.0 | 2.0 | 0.5 | 1.0 |
| His | 5.0 | 5.0 | 5.0 | 9.0 | 5.0 | 5.0 |
| Pro | 5.0 | 5.0 | 5.0 | 9.0 | 5.0 | 5.0 |
| Ser | 1.7 | 3.0 | 3.0 | 3.0 | 1.7 | 3.0 |
| Tyr | 0.4 | 0.5 | 0.5 | 0.5 | 0.4 | 0.5 |
| Gly | 7.0 | 5.9 | 5.0 | 13.0 | 7.0 | 5.9 |
| Tau | 0 | 0 | 3.5 | 7.5 | 0 | 0 |
| Leu-Ile | 6.8 | 0 | 0 | 0 | 0 | 0 |
| Ile-Leu | 0 | 14.9 | 0 | 0 | 0 | 0 |
| Leu-Val | 0 | 0 | 0 | 39.3 | 17.7 | 0 |
| Val-Leu | 0 | 0 | 31.5 | 0 | 0 | 15.7 |
| E/N | 1.72 | 1.51 | 1.70 | 1.74 | 1.72 | 1.51 |
| BCAA/TAA | 0.36 | 0.32 | 0.41 | 0.40 | 0.36 | 0.32 |
| Ile: | 1: | 1: | 1: | 1: | 1: | 1: |
| Leu: | 2: | 2: | 1.7: | 2: | 2: | 2: |
| Val | 1 | 1 | 1.3 | 1 | 1 | 1 |

TEST EXAMPLE 13

Using SD strain male rats weighing 170-180 g, a silicone rubber catheter was held in the right upper great vein under anesthetized condition, through which an infusion solution was given for a week under the intravenous hyperalimentation control (total calorie: 332 Kcal/Kg/day, nitrogen: 1.83 gN/Kg/day). The nutrient infusion solutions given had different amino acid compositions but glucose, electrolytes, vitamins and trace elements were identical. The amino acid infusion solutions tested were those infusion solutions shown in Examples 21-23 and 25-27, and, as comparative infusion solutions, infusion solutions A and B having compositions shown in Table 26 below were used.

TABLE 26

| Amino Acids | Comparative Infusion Solutions (g/l) | |
|---|---|---|
| | A | B |
| Ile | 5.6 | 8.5 |
| Leu | 12.5 | 13.5 |
| Lys | 8.8 | 8.0 |
| Met | 3.5 | 3.9 |
| Phe | 9.4 | 7.7 |
| Thr | 6.5 | 4.8 |
| Trp | 1.3 | 1.6 |
| Val | 4.5 | 9.0 |
| Ala | 6.2 | 8.6 |
| Arg | 7.9 | 11.1 |
| Asp | 3.8 | 0.5 |
| Cys | 1.0 | 1.0 |
| Glu | 6.5 | 0.5 |
| His | 6.0 | 4.7 |

TABLE 26-continued

| Amino Acids | Comparative Infusion Solutions (g/l) | |
|---|---|---|
| | A | B |
| Pro | 3.3 | 6.4 |
| Ser | 2.2 | 4.2 |
| Tyr | 0.35 | 0.5 |
| Gly | 10.7 | 5.5 |

The results are shown in Table 27. The amino acid infusion solutions of the present invention showed excellent effects with respect to body weight increase and nitrogen balance of the tested animals, as compared to the comparative infusion solutions.

TABLE 27

| Amino Acid Infusion Solutions | Gain in Body Weight (g/7 days) | Nitrogen Balance (mg N/day) |
|---|---|---|
| Example 21 | 10.0 | 101.2 |
| Example 22 | 11.0 | 110.0 |
| Example 23 | 10.5 | 101.5 |
| Example 25 | 11.2 | 111.5 |
| Example 26 | 10.3 | 100.0 |
| Example 27 | 11.0 | 110.5 |
| Comparative Solution A | 5.5 | 85.5 |
| Comparative Solution B | 6.2 | 98.0 |

As is evident from the foregoing, especially from the examples and test example, the present invention is directed to amino acid compositions which can exhibit excellent nutrient effects in various diseases and can provide highly dense amino acid infusion solutions without any preparatory restrictions. In other words, since the branched chain amino acids are used in the form of water soluble dipeptides, compositions containing the branched chain amino acid components in a high formulation proportion can be provided to be suited for the respective intended purposes.

The nutrient infusion solutions of the present invention can exhibit excellent nutrient effects in various diseases, as amino acid infusion solutions for respective diseases or for general purpose.

The dipeptide in accordance with the present invention is effectively utilized in the living body.

A Fifth Embodiment:

In order to solve the fourth problem described above, the present inventors have made investigations and as a result, have found that branched chain L-amino acid compositions which contain dipeptide(s) of BCAA are provided for amino acid infusion solution. That is, according to the present invention, the problem in preparations described above can be solved by replacing a part or the whole of Leu, Ile and/or Val with dipeptide(s) whose molecules contain at least one branched chain L-amino acid residue, for example, L-leucyl-L-isoleucine (Leu-Ile, L-isoleucyl-L-leucine (Ile-Leu), L-leucyl-L-valine (Leu-Val), L-valyl-L-leucine (Val-Leu), L-isoleucyl-L-valine (Ile-Val) and L-valyl-L-isoleucine (Val-Ile). Thus, amino acid infusion solutions for intravenous administration which contain the branched chain L-amino acids (BCAA) at a high concentration in a ratio suited for the intended purpose and have an excellent ratio of Leu, Ile and Val formulated can be prepared with the use of the BCAA compositions of the present invention. The present invention has thus been accomplished on the basis of these findings.

That is, the present invention is to provide, in a fifth embodiment, a branched chain L-amino acid composition containing at least one dipeptide whose molecules contain at least one branched chain L-amino acid residue for amino acid infusion solutions, which composition is characterized in that the concentration of Leu has been adjusted to 20–100 g/l in the L-amino acid components including the respective component L-amino acids if said dipeptide is calculated as the respective component L-amino acids.

It is preferred that when the dipeptide is calculated as L-amino acids in a BCAA composition containing at least one dipeptide whose molecules contain at least one branched chain L-amino acid residue for amino acid infusion solutions, at least the amino acids indicated in Table 28 below are contained in the composition ranges indicated therein and the weight ratio of Leu, Ile and Val is in the range of 1.6–2.4 : 0.8–1.2 : 0.8–1.2 from the sitological point of view.

TABLE 28

| Amino Acid | Composition Range (g/l) |
|---|---|
| Leu | 20.0–100.0 |
| Ile | 10.0–50.0 |
| Val | 10.0–50.0 |

The term "when the dipeptide is calculated as L-amino acids" described above means that "when an amount of the dipeptide is calculated as the amounts of the respective L-amino acids formed when the said dipeptide is fully hydrolyzed".

The amino acid composition shown in Table 28 is determined from the preparatory and sitological point of view.

Examples of dipeptides containing at least one branched chain L-amino acid residue which can be used in the present invention include Leu-Ile, Ile-Leu, Leu-Val, Val-Leu, Ile-Val, Val-Ile, as has been mentioned above.

In a BCAA composition of the present invention, the ratio of the BCAA in the free state and the BCAA in the dipeptide(s) form is 0–100 : 4–300.

The composition of the present invention cannot be used as an amino acid infusion solution as it is. However, as will be shown below, amino acid infusion solutions suitable for particular morbid conditions can readily be prepared by mixing the composition of the present invention with other amino acid compositions in an appropriate ratio.

Desired amino acid infusion solutions can be prepared conventionally in a manner similar to known amino acid infusion solutions except a composition of the present invention is used. Any pH value can be taken but preferred is between 4.5 and 8.0 from the physiological point of view.

Furthermore, nutrient substances such as sugars, vitamins, minerals, etc may also be incorporated utilizing known techniques. Even when reducing sugars are formulated in the amino acid infusion compositions, it is difficult to cause the Maillard reaction and in this sense, the compositions are advantageous The present invention will be described in more detail by referring to the examples and preparation examples below.

EXAMPLE 29

The branched chain amino acids and dipeptides containing the branched chain amino acid residues shown in Table 29 below were dissolved in distilled water for injection by heating to make the whole volume 0.99 liter. After adjusting its pH to 6.0 to 7.0 with an aqueous acetic acid solution, the whole volume was made 1 liter. The solution was filtered through a membrane filter having a pore diameter of 0.45 $\mu$. The filtrate was filled in a 200 ml glass bottle. After replacing the air with nitrogen gas, the bottle was tight-sealed. This was sterilized with steam under high pressure to prepare a BCAA composition, which was supposed to be used in preparing amino acid infusion solutions.

The composition of this example contained 30.0 g/l of Ile, 50.0 g/l of Leu and 25.0 g/l of Val.

TABLE 29

| Amino Acid and Dipeptide | Amount Used (g/l) |
|---|---|
| Ile | 10.0 |
| Leu | 10.0 |
| Val | 7.1 |
| Leu-Ile | 37.3 |
| Leu-Val | 35.1 |

In Examples 30–44, BCAA compositions to be used for amino acid infusion solutions were prepared in a conventional manner using dipeptides containing branched chain L-amino acid residues and/or branched chain L-amino acids indicated in Tables 30–44, respectively.

EXAMPLE 30

TABLE 30

| Amino Acid and Dipeptide | Amount Used (g/l) |
|---|---|
| Ile | 5.0 |
| Leu | 10.0 |
| Val | 12.1 |
| Ile-Leu | 37.3 |
| Val-Leu | 35.1 |

The composition of this example contained 25.0 g/l of Ile, 50.0 g/l of Leu and 30.0 g/l of Val.

EXAMPLE 31

TABLE 31

| Amino Acid and Dipeptide | Amount Used (g/l) |
|---|---|
| Ile | 5.0 |
| Leu | 10.0 |
| Val | 7.1 |
| Leu-Ile | 37.3 |
| Val-Leu | 35.1 |

The composition of this example contained 25.0 g/l of Ile, 50.0 g/l of Leu and 25.0 g/l of Val.

EXAMPLE 32

TABLE 32

| Amino Acid and Dipeptide | Amount Used (g/l) |
|---|---|
| Ile | 10.0 |
| Leu | 10.0 |
| Val | 12.1 |
| Ile-Leu | 74.5 |
| Leu-Val | 35.1 |

The composition of this example contained 50.0 g/l of Ile, 70.0 g/l of Leu and 30.0 g/l of Val.

EXAMPLE 33

TABLE 33

| Amino Acid and Dipeptide | Amount Used (g/l) |
|---|---|
| Ile | 10.0 |
| Leu | 20.0 |
| Val | 20.0 |
| Leu-Ile | 37.3 |

The composition of this example contained 30.0 g/l of Ile, 40.0 g/l of Leu and 20.0 g/l of Val.

TABLE 34

| Amino Acid and Dipeptide | Amount Used (g/l) |
|---|---|
| Leu | 20.0 |
| Val | 25.0 |
| Leu-Ile | 46.6 |

The composition of this example contained 25.0 g/l of Ile, 45.0 g/l of Leu and 25.0 g/l of Val.

EXAMPLE 35

TABLE 35

| Amino Acid and Dipeptide | Amount Used (g/l) |
|---|---|
| Val | 2.1 |
| Ile-Leu | 37.3 |
| Leu-Val | 35.1 |

The composition of this example contained 20.0 g/l of Ile, 40.0 g/l of Leu and 20.0 g/l of Val.

EXAMPLE 36

TABLE 36

| Amino Acid and Dipeptide | Amount Used (g/l) |
|---|---|
| Val | 0.1 |
| Leu-Ile | 27.9 |
| Val-Leu | 35.1 |

The composition of this example contained 15.0 g/l of Ile, 35.0 g/l of Leu and 18.0 g/l of Val.

EXAMPLE 37

TABLE 37

| Amino Acid and Dipeptide | Amount Used (g/l) |
|---|---|
| Leu | 15.0 |
| Val | 15.0 |
| Ile-Leu | 27.9 |

The composition of this example contained 15.0 g/l of Ile, 30.0 g/l of Leu and 15.0 g/l of Val.

EXAMPLE 38

TABLE 38

| Amino Acid and Dipeptide | Amount Used (g/l) |
|---|---|
| Leu | 10.0 |
| Val | 10.0 |
| Ile-Leu | 18.6 |

The composition of this example contained 10.0 g/l of Ile, 20.0 g/l of Leu and 10.0 g/l of Val.

EXAMPLE 39

TABLE 39

| Amino Acid and Dipeptide | Amount Used (g/l) |
|---|---|
| Leu | 20.0 |
| Val | 15.5 |
| Leu-Ile | 37.3 |
| Ile-Val | 8.8 |

The composition of this example contained 25.0 g/l of Ile, 40.0 g/l of Leu and 20.0 g/l of Val.

EXAMPLE 40

TABLE 40

| Amino Acid and Dipeptide | Amount Used (g/l) |
|---|---|
| Leu | 20.0 |
| Val | 1.1 |
| Val-Ile | 17.6 |

The composition of this example contained 10.0 g/l of Ile, 20.0 g/l of Leu and 10.0 g/l of Val.

EXAMPLE 41

TABLE 41

| Amino Acid and Dipeptide | Amount Used (g/l) |
|---|---|
| Leu | 20.0 |
| Val | 1.6 |
| Ile-Val | 26.3 |

The composition of this example contained 15.0 g/l of Ile, 20.0 g/l of Leu and 15.0 g/l of Val.

EXAMPLE 42

TABLE 42

| Amino Acid and Dipeptide | Amount Used (g/l) |
|---|---|
| Ile | 10.0 |
| Leu | 10.0 |
| Val | 12.1 |
| Leu-Ile | 74.5 |
| Val-Leu | 35.1 |

The composition of this example contained 50.0 g/l of Ile, 70.0 g/l of Leu and 30.0 g/l of Val.

EXAMPLE 43

TABLE 43

| Amino Acid and Dipeptide | Amount Used (g/l) |
|---|---|
| Leu-Ile | 37.3 |
| Leu-Val | 35.1 |

The composition of this example contained 20.0 g/l of Ile, 40.0 g/l of Leu and 17.9 g/l of Val.

EXAMPLE 44

TABLE 44

| Amino Acid and Dipeptide | Amount Used (g/l) |
|---|---|
| Leu-Ile | 74.5 |
| Leu-Val | 70.2 |

The composition of this example contained 40.0 g/l of Ile, 80.0 g/l of Leu and 35.8 g/l of Val.

PREPARATION EXAMPLES 1-5

Portions of the BCAA composition obtained in Example 31 were mixed with a commercially available amino acid infusion solution in various ratios in a conventional manner. Thus, amino acid infusion solutions 1-5 were prepared.

The compositions of the amino acids in the infusion solutions thus prepared are shown in Table 45.

TABLE 45

| | Composition of Amino Acids after Mixing | | | | |
|---|---|---|---|---|---|
| | Preparation Example No. | | | | |
| | 1 | 2 | 3 | 4 | 5 |
| | Mixing Ratio | | | | |
| | 0.5:1 | 1:1 | 0.1:1 | 0.1:1 | 0.1:1 |
| Ile | 11.8 | 15.0 | 7.1 | 11.5 | 10.5 |
| Leu | 24.2 | 30.7 | 15.4 | 19.3 | 16.3 |
| Lys | 8.1 | 6.1 | 10.9 | 13.8 | 6.5 |
| Met | 2.3 | 1.7 | 3.1 | 13.4 | 4.0 |
| Phe | 6.1 | 4.6 | 8.2 | 13.4 | 6.4 |
| Thr | 4.2 | 3.2 | 5.7 | 6.1 | 6.8 |
| Trp | 0.85 | 0.63 | 1.1 | 3.0 | 1.2 |
| Val | 11.1 | 14.5 | 6.2 | 12.1 | 15.0 |
| Ala | 4.0 | 3.0 | 5.5 | 6.7 | 6.5 |
| Arg | 5.1 | 3.9 | 7.0 | — | 8.2 |
| Asp | 2.5 | 1.9 | 3.3 | — | 0.91 |
| Cys | 0.65 | 0.49 | 0.88 | — | — |
| Glu | 4.2 | 3.2 | 5.7 | — | 0.45 |
| His | 3.9 | 2.9 | 5.3 | — | 4.5 |
| Pro | 2.1 | 1.6 | 2.9 | — | 4.5 |
| Ser | 1.4 | 1.1 | 1.9 | — | 1.5 |
| Tyr | 0.22 | 0.17 | 0.31 | — | 0.36 |
| Gly | 7.0 | 5.3 | 9.4 | — | 6.4 |

Preparations Nos. 1, 2 and 5 in the table above were obtained by mixing the BCAA composition with a commercially available amino acid infusion solution in ratios of 0.5 : 1, 1 : 1 and 0.1 : 1, in which preparations the content of branched chain L-amino acids was relatively high and the glycine content was relatively suppressed low since glycine tends to cause hyperammonemia. These preparations are suitably administered to patients in the post-operative stage or patients without any abnormality in amino acid metabolism.

Preparation No. 3 described above was obtained by mixing the BCAA composition with the commercially available amino acid infusion solution in a ratio of 0.1 : 1, in which preparation branched chain amino acids metabolized in organs other than liver were contained in large quantities. The preparation can improve nutritious conditions of patients with hepatic disorder.

Preparation No. 4 described above was obtained by mixing the BCAA composition with the same amino acid infusion solution in a ratio of 0.1 : 1, in which preparation the content of non-essential L-amino acids was reduced so as to re-use blood urea and ammonia for synthesis of L-amino acids. The preparation is suited for administration to patients with renal disorder.

Thus, it is understood that by appropriately changing the mixing ratio as described above, amino acid infusion solutions having desired compositions can readily be obtained by using BCAA compositions of the present invention.

As is evident especially from the foregoing examples and preparation examples, the BCAA composition of the present invention contains branched chain L-amino acids in a high concentration in a suitable ratio and is useful as a premixing preparation for preparing amino acid infusion solutions for respective morbid conditions which are required to administer highly dense branched chain L-amino acids. In other words, if a conventional amino acid infusion solution is mixed with a BCAA composition of the present invention in an appropriate ratio, then amino acid infusion solutions oan readily be prepared which solutions are suited for respective specific diseases.

According to the present invention, since branched chain L-amino acids are in the form of dipeptides, compositions for amino acid infusion solutions can be provided in a ratio suited for the intended purposes, without any preparatory restrictions. The composition of the present invention is useful as a composition which can be formulated in amino acid infusion solutions used for respective morbid conditions.

The dipeptides in accordance with the present invention are effectively utilized in the living body.

What is claimed is:

1. In an aqueous nutrient infusion solution comprising an effective amount of essential L-amino acids, including L-tryptophan, the improvement therein being that (a) substantially all of said L-tryptophan is in the form of L-tryptophyl-L-alanine or L-tryptophyl-L-leucine or mixtures thereof and (b) wherein said solution does not have a stabilizer as an ingredient thereof.

2. The nutrient infusion solution according to claim 1 comprising
  (a) at least one dipeptide selected from the group consisting of L-tryptophyl-L-alanine and L-tryptophyl-L-leucine; and
  (b) at least one amino acid selected from the group consisting of L-isoleucine, L-leucine, L-lysine, L-methionine, L-phenylalanine, L-threonine, L-valine, L-alanine, L-arginine, L-aspartic acid, L-cysteine, L-glutamic acid, glycine, L-histidine, L-ornithine, L-proline, L-serine and L-tyrosine; and failing to have a stabilizer as an ingredient thereof.

* * * * *